(12) United States Patent
Coon

(10) Patent No.: US 8,491,542 B2
(45) Date of Patent: Jul. 23, 2013

(54) LIGHT WEIGHT TUBE CLAMP FOR MEDICAL FLUIDS

(75) Inventor: Zachary A. Coon, Plymouth, MI (US)

(73) Assignee: Terumo Cardiovascular Systems Corp., Ann Arbor, MI (US)

( * ) Notice: Subject to any disclaimer, the term of this patent is extended or adjusted under 35 U.S.C. 154(b) by 311 days.

(21) Appl. No.: 13/041,904

(22) Filed: Mar. 7, 2011

(65) Prior Publication Data
US 2012/0232495 A1 Sep. 13, 2012

(51) Int. Cl.
*A61M 5/00* (2006.01)
*F16K 7/04* (2006.01)
*F16K 31/00* (2006.01)

(52) U.S. Cl.
USPC ............... 604/250; 604/256; 251/7; 251/294

(58) Field of Classification Search
None
See application file for complete search history.

(56) References Cited

U.S. PATENT DOCUMENTS

| 4,818,177 A | 4/1989 | Grohmann |
| 5,445,613 A | 8/1995 | Orth |
| 5,626,059 A * | 5/1997 | Bobbitt et al. ................. 74/493 |
| 6,386,505 B2 | 5/2002 | Schöb |
| 7,367,540 B2 | 5/2008 | Brieske |

* cited by examiner

*Primary Examiner* — Bhisma Mehta
*Assistant Examiner* — Lauren M Peng
(74) *Attorney, Agent, or Firm* — Gael Diane Tisack, Esq.; Darryl Newell; McMillan, Sobanski & Todd

(57) ABSTRACT

A tube clamping system includes a Bowden cable with an inner member and an outer casing. A first jaw element has a first tube abutment surface, a passage, and a first sliding latch portion. The inner member passes through the passage. A second jaw element has a second tube abutment surface, a cable guide, and a second sliding latch portion. The inner member has a first end held in the mated sliding latch portions so that sliding of the inner member results in selectably positioning the first and second tube abutment surfaces together or spaced apart. An actuator coupled to a second end of the outer casing and a second end of the inner member applies a force to slide the inner member within the outer casing, the passage, and the cable guide. The Bowden cable substantially isolates the tube being clamped from the weight of the actuator.

12 Claims, 6 Drawing Sheets

LIGHT WEIGHT TUBE CLAMP FOR MEDICAL FLUIDS

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to a fast clamp occluder for medical fluid applications, and, more specifically, to a light weight clamp particularly useful for clamping a blood circuit in a blood perfusion system.

During cardiac bypass surgery, the heart is stopped in order to allow repair of defects, such as the replacement of defective heart valves, or the placement of bypass grafts. The patient's blood is redirected through an extracorporeal perfusion circuit typically including various items such as a venous cannula, flexible PVC tubing, a reservoir, a pump, an oxygenator, an arterial filter, and an arterial cannula. During extraction of blood from the patient and/or at various stages of flow within the perfusion circuit, air emboli may form within the circulating blood. If these emboli are not removed from the circulating blood and are instead introduced back to the patient's bloodstream, there may be serious complications.

An occluder (i.e., a clamp) is typically arranged around the tubing to function as a shutoff valve. It can be quickly actuated whenever emboli are detected in the blood so that blood flow is stopped before any emboli reach the patient. The occluder of present invention is also useful in connection with other procedures in which medical fluids flow through deformable tubing wherein the flow may be stopped by clamping down on the tubing.

Conventional clamps have included various electromagnetic and pneumatic devices designed to achieve very fast closing times. In order to generate and direct the forces necessary to achieve the fast closing times, conventional clamps have been relatively massive. Due to their weight, the clamping systems have typically required mounting support such as brackets suspended from a pole or fixture. The need for such a support limits the locations on the tubing of the blood circuit where the clamp can be conveniently installed, and it complicates the set-up of the perfusion circuit.

A typical electromagnetic clamp design passes the flexible tubing between a solenoid plunger and a wall surface. By activating the solenoid, the tubing is pinched against the wall to stop the fluid flow. If the tubing is not properly aligned with the plunger, however, the tubing may not become completely pinched off and there may be leakage.

SUMMARY OF THE INVENTION

The present invention provides a light weight clamp that is self-supporting so that it can be positioned practically anywhere on a tubing circuit. Pressure is always applied evenly across the clamp so that there are no problems associated with misalignment or even application of clamping forces to the tubing.

In one aspect of the invention, a clamp system selectably clamps a tube carrying medical fluid. The system includes a Bowden cable having an inner member slidable within an outer tubular casing. A first jaw element has a first tube abutment surface, a passage extending through the first jaw element generally perpendicular to the first tube abutment surface, and a first sliding latch portion. The first tube abutment surface is disposed between the passage and the first sliding latch portion. The outer tubular casing has a first end fixedly mounted with respect to the first jaw element. The inner member of the Bowden cable passes through the passage. A second jaw element has a second tube abutment surface, a substantially semi-circular cable guide receiving the inner member of the Bowden cable, and a second sliding latch portion for mating with the first sliding latch portion. The inner member has a first end which is held in the mated sliding latch portions so that sliding of the inner member results in selectably positioning the first and second tube abutment surfaces together or spaced apart. An actuator is coupled to a second end of the outer tubular casing and a second end of the inner member for applying a force to slide the inner member within the outer tubular casing, the passage, and the cable guide. The Bowden cable substantially isolates the tube being clamped from the weight of the actuator.

DETAILED DESCRIPTION OF PREFERRED EMBODIMENTS

In the present invention, a clamp is remotely driven by a motor via a Bowden cable. Consequently, the clamp can be fully supported by the tube with no need for external brackets. The invention permits the clamp to be placed well away from the motor in places not previously allowed when bracketed support was needed, while the heavier motor portion can be placed and supported in a location which is less obtrusive than the clamping locations used in conventional clamps. Furthermore, the Bowden cable design of the invention provides equal force on both sides of the tube to ensure that the jaws stay parallel and that any misalignment of the tube will not affect the evenness of the pressure applied to occlude the tube.

Figure 1:
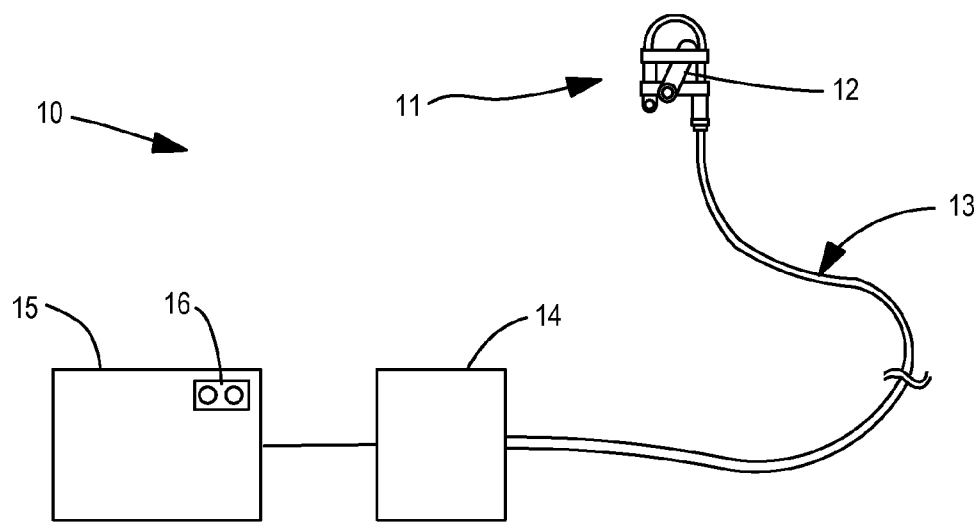
FIG. 1 is a schematic diagram of a clamp system according to one embodiment of the invention.

Referring now to FIG. 1, a clamp system 10 includes a clamp device 11 holding a portion of a tube 12 carrying a medical fluid such as blood in a profusion system. Clamp device 11 is connected via a Bowden cable 13 to an actuator or driver 14. A control panel 15 for a perfusion system is connected to actuator 14 for electrically controlling actuator 14 in a desired manner to selectably control the Bowden cable and the position of clamp device 11. Controller 15 may preferably connect to sensors (not shown) such as an emboli or bubble sensor to automatically determine that clamp device 11 should be closed. In addition, manual controls 16 may be provided on controller 15 for manually selecting a fully clamped or an unclamped position of clamp device 11 (or any intermediate position, if desired). Because of its light weight and because it is isolated from the weight of actuator 14 by Bowden cable 13, clamp device 11 can be located at any desirable location along tube 12.

Figure 2:
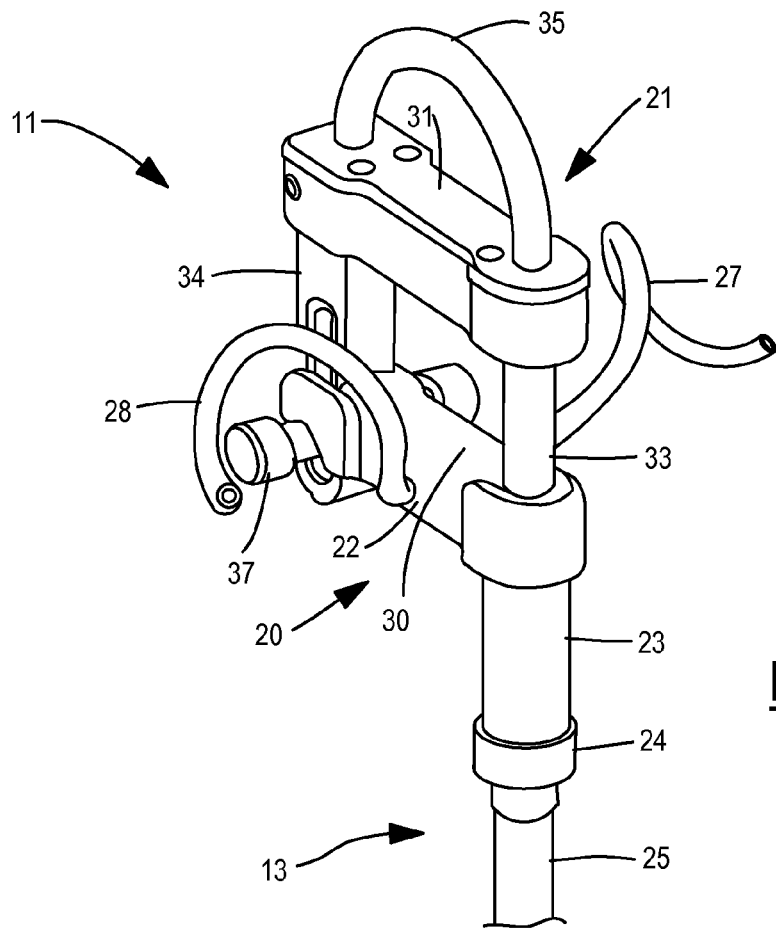
FIG. 2 is a perspective view of a first embodiment of a clamp.
Figure 3:
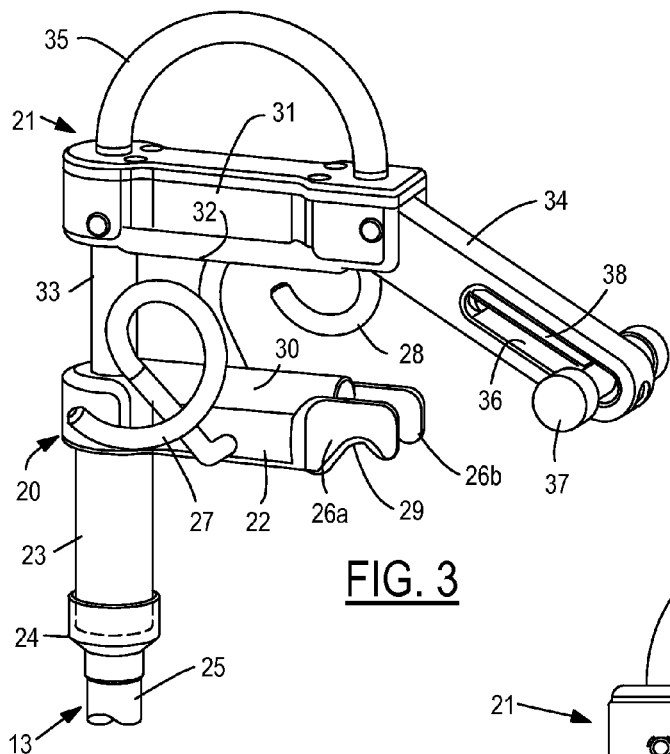
FIG. 3 shows the clamp of FIG. 2 in an open position for receiving a tubing section.

A first embodiment of clamp device 11 is shown in FIGS. 2-11. FIGS. 2 and 3 show perspective views of clamp device 11, wherein clamp device 11 is in a closed and unclamped position in FIG. 2 and is in an open and unclamped position in FIG. 3. The open position allows for receiving a section of tubing into device 11. A lower jaw element 20 is slidably connected to an upper jaw element 21. Lower jaw element 20 has a bar member 22 and a cylindrical member 23 joined at substantially a right angle. A fitting 24 at the lower end of cylindrical member 23 serves to receive Bowden cable 13, in particular so that an outer casing 25 of Bowden cable 13 terminates at fitting 24. Bar member 22 has a first sliding latch portion comprised of a pair of spaced extensions 26a and 26b which share a common catch groove 29 on their bottom surface. A top surface of bar member 22 provides a first tube abutment surface 30. A pair of pigtail clips 27 and 28 extend from the sides of bar member 22 for receiving and aligning a tube substantially transversely to first tube abutment surface 30.

Upper jaw element 21 includes a bar member 31 with a bottom side that provides a second tube abutment surface 32. An alignment rod 33 is mounted to bar member 31 and is slidably received within cylindrical member 23 of lower jaw element 20. At the other end of bar member 31, upper jaw element 21 includes a swing arm 34 which is pivotably attached to bar member 31 at one end. Generally at the other end of swing arm 34, a slot 36 slidably receives a latch bar 37. An inner sliding member 38 of the Bowden cable passes through lower jaw element 20 and alignment rod 33, and further through a cable guide 35 in the form of a semi-circular curved tube. An end of inner sliding member 38 is attached to latch bar 37 so that inner sliding member 38 can be used to control the position of latch bar 37 in slot 36. As shown in FIG. 3, when latch bar 37 is moved toward the lower end of slot 36 by extending inner member 38 of the Bowden cable, the resulting clearance between latch bar 37 and groove 29 allows swing arm 34 to move freely into an open position so that a tube may be brought between abutment surfaces 30 and 32. The tube may be maneuvered into pigtail clips 27 and 28 in order to maintain better alignment.

Figure 4:
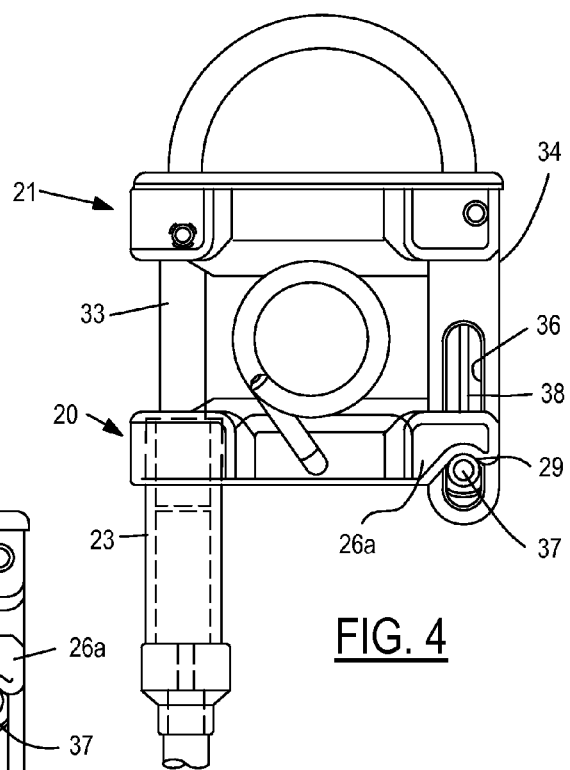
FIG. 4 is a side view of the clamp of FIG. 2 in an unclamped position.
Figure 5:
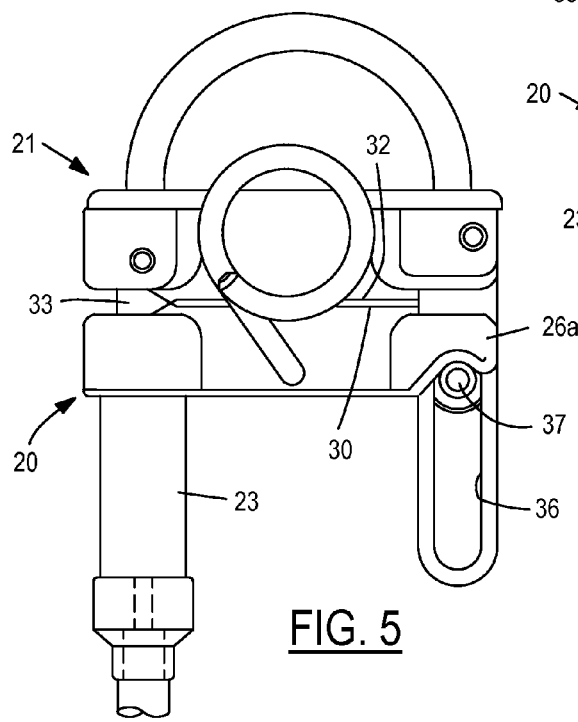
FIG. 5 is a side view of the clamp of FIG. 2 in a clamped position.

As shown on FIGS. 4 and 5, upper and lower jaws 20 and 21 are relatively slidable to control the separation distance between tube abutment surfaces 30 and 32 between a fully spaced apart position (i.e., unclamped) shown in FIG. 4 and a contacting position (i.e., clamped) shown in FIG. 5. The jaw elements latch together to enclose a tube within device 11 by the action of a latch comprising first and second latch portions. The first latch portion is comprised of latch bar 37 connected to the end of inner member 38 of the Bowden cable mounted in swing arm 34. The second latch portion is comprised of extensions 26a and 26b and catch groove 29. Swing arm 34 enters between extensions 26a and 26b and latch bar 37 is captured in catch groove 29 to close the latch. By applying a pulling force to inner member 28 of the Bowden cable, upper jaw member 21 is drawn downward toward lower jaw element 20 so that a tube located between abutment surfaces 30 and 32 is progressively squeezed until its fluid passage is completely blocked off.

Figure 6:
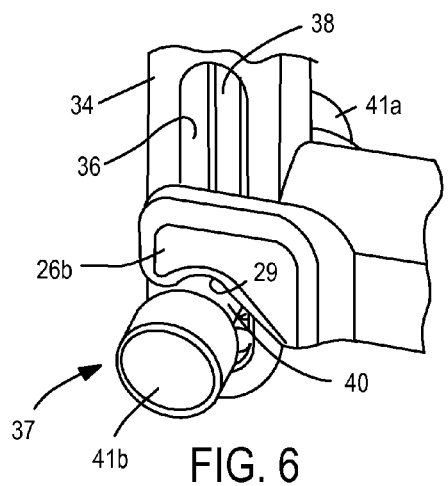
FIG. 6 shows the latch of the clamp in greater detail.

The latching of the upper and lower jaw elements 20 and 21 is shown in greater detail in FIG. 6. Spaced-apart extensions 26a and 26b receive swing arm 34 to allow latch pin 37 to enter catch groove 29. To help provide positive retention, latch pin 37 includes a central shaft 40 between enlarged ends 41a and 41b.

Figure 7:
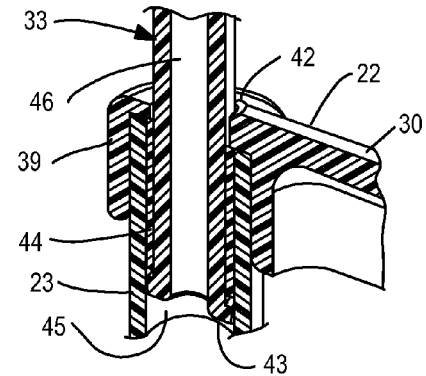
FIG. 7 shows the alignment rod of the clamp in greater detail.

The sliding of alignment rod 33 within the lower jaw element is shown in greater detail in FIG. 7. Cylindrical member 23 is retained in a cup 29 of bar element 22. Alignment rod 33 extends through a hole 42 in bar member 22 and into the interior passageway 45 of cylindrical member 23. Alignment rod 33 includes an out-turned flange 43 at its end with an increased diameter. A bearing sleeve 44 is retained between alignment rod 33 and cylindrical member 23 in a space above flange 43. Alignment rod 33 has an internal passage 46 aligned with passage 45 of cylindrical member 23, both of which receive inner member 38 of the Bowden cable.

Figure 8:
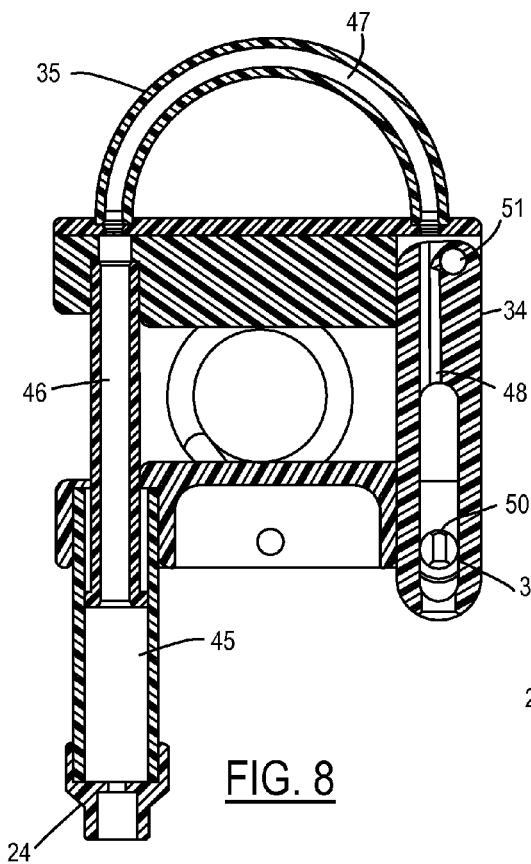
FIG. 8 is a cross section of the clamp of FIG. 2 in an unclamped position.
Figure 9:
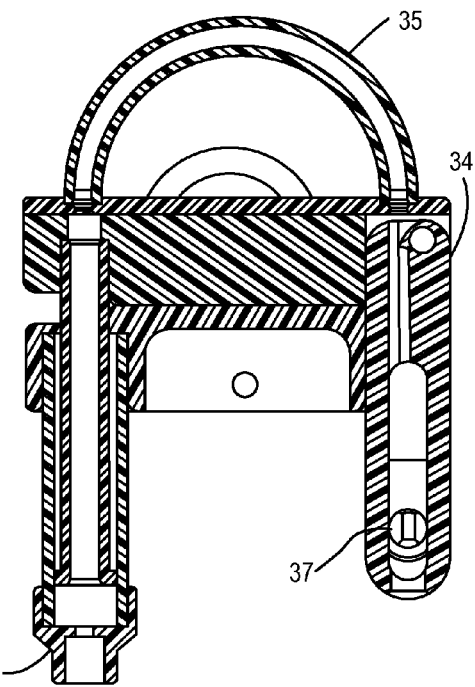
FIG. 9 is a cross section of the clamp of FIG. 2 in a clamped position.

FIG. 8 is a cross-section showing the complete passageway through which the inner member of the Bowden cable passes from fitting 24 to latch bar 37. Thus, a continuous pathway is provided through passage 45, passage 46, a passage 47 within cable guide 35, and a passage 48 within swing arm 34. Latch bar 37 may also have an internal passage 50 where the inner member of the Bowden cable is attached. The cross-section of FIG. 8 further shows a pivot 51 around which swing arm 34 rotates. As seen in the cross-section of FIG. 9, when the clamp device is in its clamping or closed position, the length of the pathway within the device for the Bowden cable is reduced as compared with the open position.

Figure 10:
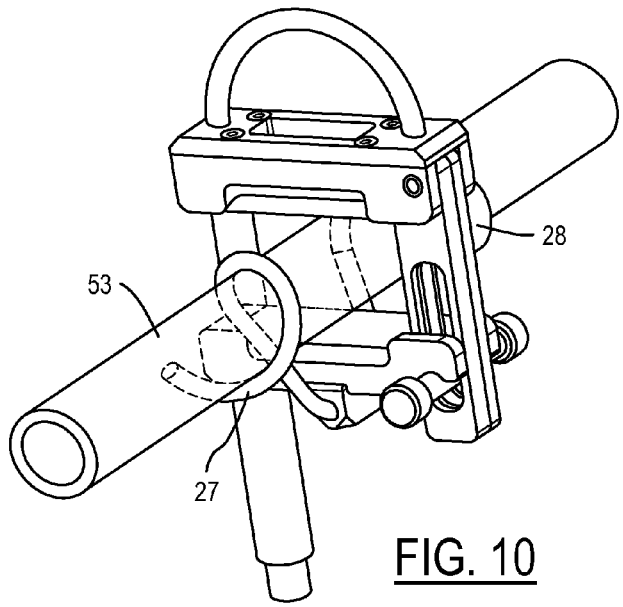
FIG. 10 shows the clamp receiving a tubing with a first diameter.
Figure 11:
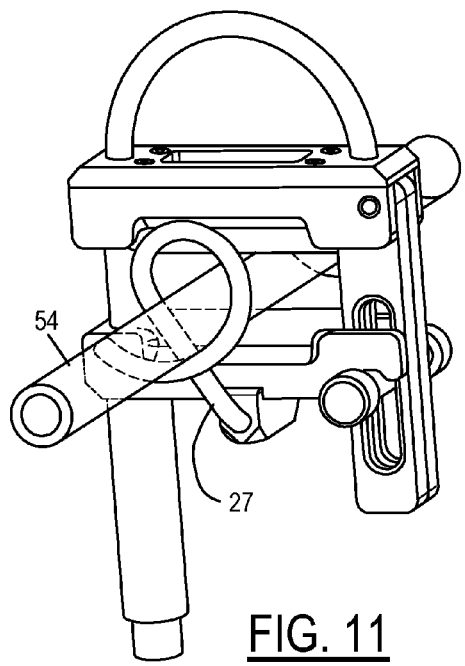
FIG. 11 shows the clamp receiving a tubing with a second diameter.

The device of the present invention can accommodate different sizes of tubing (e.g., different diameters). As shown in FIG. 10, pigtail clips 27 and 28 are shaped to accommodate a certain maximum tubing size. For example, a tube 53 comprised of PVC tubing with a ½ inch outside diameter and 3⁄32 inch wall thickness matches the inner diameter of clips 27 and 28. With the same clamp, a smaller tubing size such as an outside diameter of ¼ inch and wall thickness of 1⁄16 inch may be occluded as shown in FIG. 11.

Figure 12:
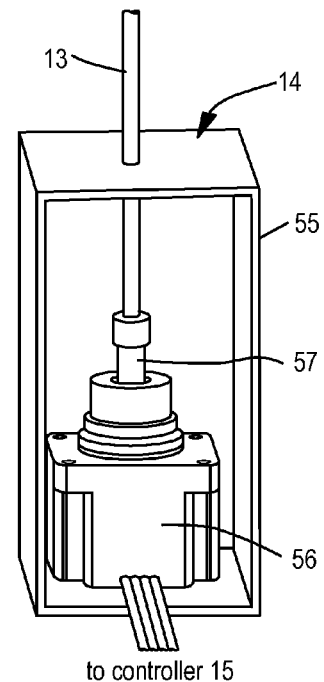
FIG. 12 shows a first embodiment of an actuator.

A first embodiment of actuator 14 is shown in FIG. 12. A motor box 55 includes a linear motor 56 having an output shaft 57 coupled to Bowden cable 13. In response to signals from controller 15, shaft 57 is extended or retracted for sliding the inner cable member of Bowden cable 13 within its outer casing whereby the clamp device is opened or closed.

Figure 13:
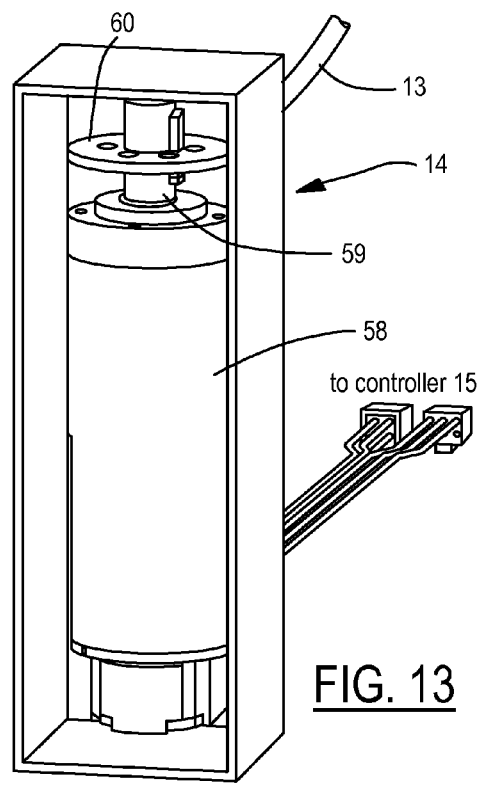
FIG. 13 shows a second embodiment of an actuator.

FIG. 13 shows an alternative embodiment using a rotary motor 58 driving a shaft 59 having a spool 60. The inner cable is attached to spool 60 for controllably retracting or extending it within the outer casing of Bowden cable 13 in response to rotation of shaft 59. Rotor 58 is connected to controller 15 to provide both automatic and manual control of the clamp.

Figure 14:
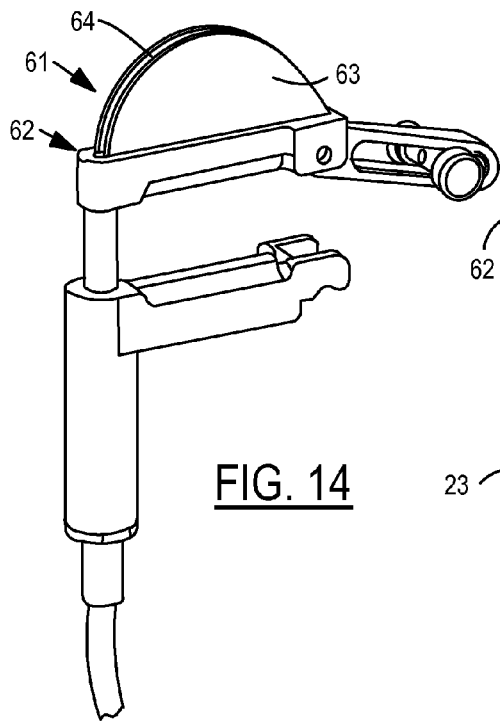
FIG. 14 is a perspective view of a second embodiment of the clamp.
Figure 15:
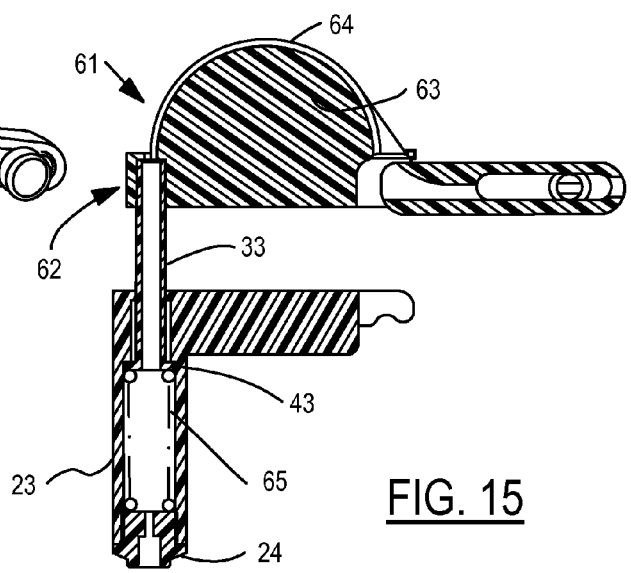
FIG. 15 is a cross section of the clamp of FIG. 14.
Figure 16:
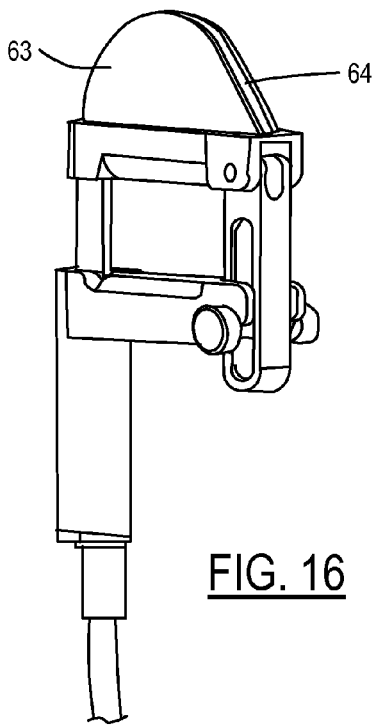
FIG. 16 is another perspective view of the clamp of FIG. 14.
Figure 17:
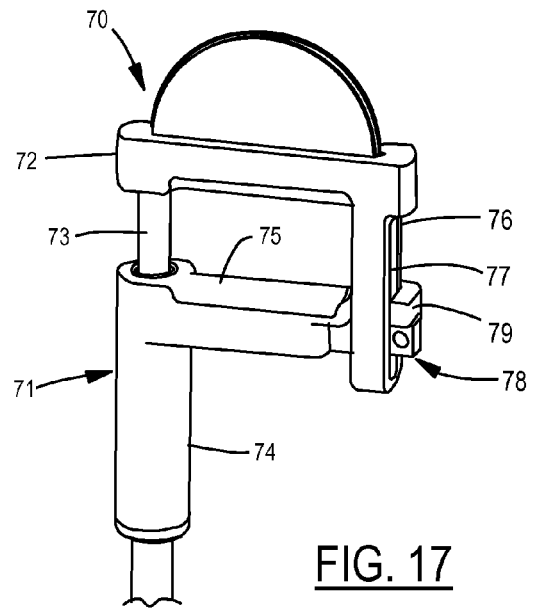
FIGS. 17, 18, and 19 are perspective views of a third embodiment of the clamp which is closed in FIG. 17 and open in FIGS. 18 and 19.
Figure 18:
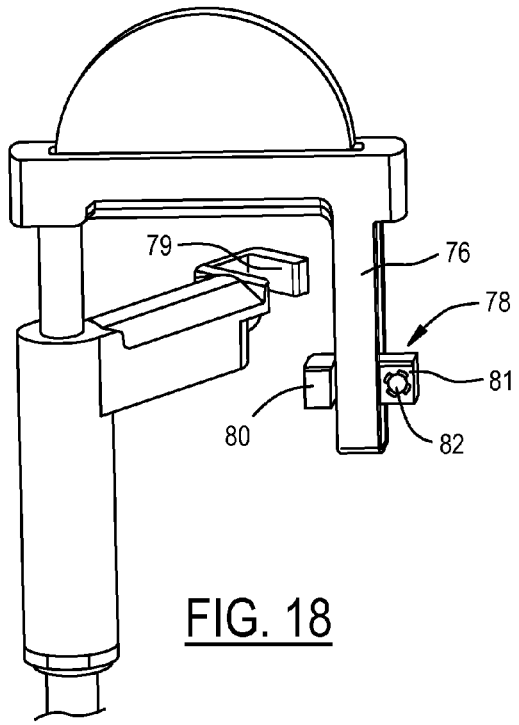
Figure 19:
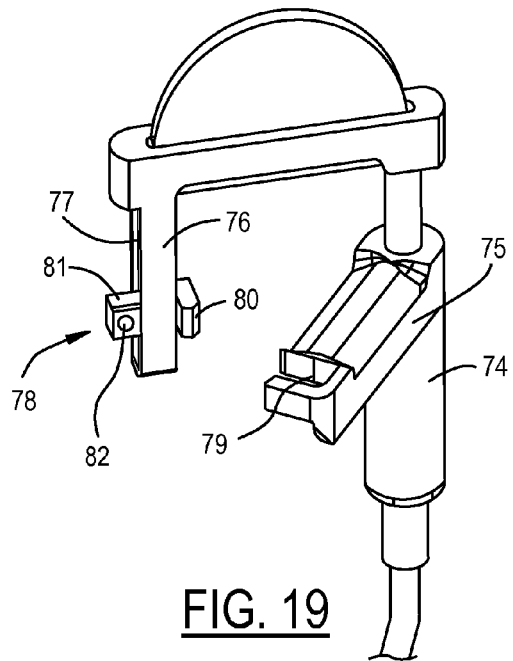

FIGS. 14-16 illustrate a second embodiment of a clamp device 61 having an upper jaw 62 with a disk-shaped plate portion 63 having a cable guide 64 therein. Cable guide 64 may preferably be enclosed within plate 63 or a supplemental cover or liner may be applied (not shown) so that the moving inner member of the Bowden cable is not exposed.

As shown in the cross-section of FIG. 15, a spring 65 may preferably be provided within cylindrical member 23 between fitting 24 and flange 43 of alignment rod 33. Spring 65 biases clamp 61 into a spaced apart position whenever a closing force is not being applied by the Bowden cable.

FIGS. 17-21 illustrate an alternative embodiment wherein a clamp device 70 is rotationally opened in order to insert a tube between a lower jaw element 71 and an upper jaw element 72. Upper jaw element 72 has an alignment rod 73 slidably retained in a cylindrical member 74 of lower jaw element 71. Lower jaw element 71 also includes a bar member 75.

Upper jaw element 72 and includes an arm 76 having a slot 77 aligned with an inner member of the Bowden cable (not shown) which connects to a latch block 78. Bar member 75 has a notch 79 at one end to receive arm 76. By rotating upper jaw element 72 with respect to lower jaw element 71 so that alignment rod 73 spins within cylindrical member 74, arm 77 is released from notch 79 allowing a tube to be inserted in the open position shown in FIGS. 18 and 19.

Figure 20:
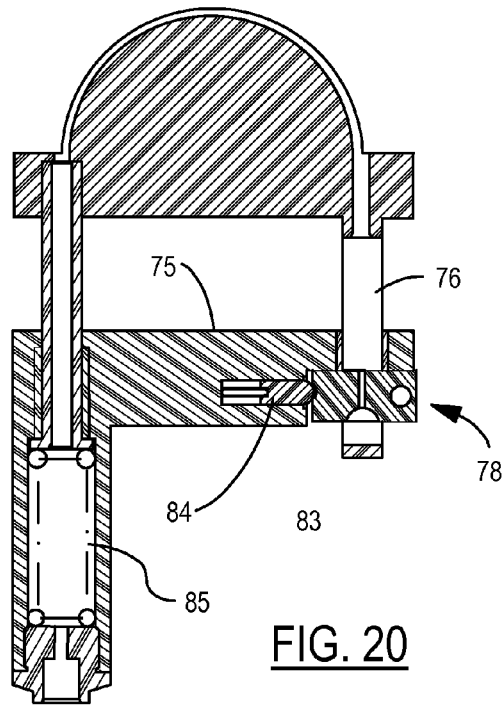
FIGS. 20 and 21 are cross-sectional views of the clamp of FIG. 17 in the unclamped and clamped positions, respectively.
Figure 21:
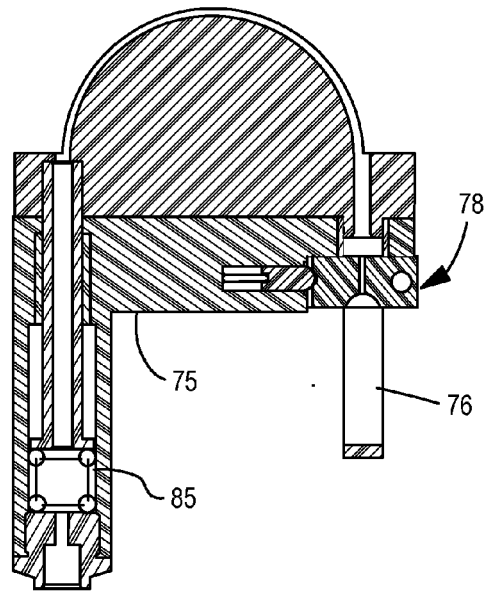

Latch block 78 includes a butt 80 on one side of slot 77 and a retention end 81. A set screw 82 or other adjustable feature retains block 78 within slot 77. Butt 80 has an interference fit with matching structure on bar member 75 in order to help retain the jaw elements in a closed position. As shown in FIGS. 20 and 21, butt 80 preferably includes a detent 83 for receiving a spring loaded plunger 84 mounted in lower jaw element 75 to thereby retain block 78 in a releasable manner.

FIGS. 20 and 21 further show the compression of a spring 85 when moving between the unclamped and clamped positions of the clamp device.

What is claimed is:

1. A clamp system for selectably clamping a tube carrying medical fluid, comprising:
    a Bowden cable having an inner member slidable within an outer tubular casing;
    a first jaw element having a first tube abutment surface, a passage extending through the first jaw element generally perpendicular to the first tube abutment surface, and a first sliding latch portion, wherein the first tube abutment surface is disposed between the passage and the first sliding latch portion, wherein the outer tubular casing has a first end fixedly mounted with respect to the first jaw element, and wherein the inner member of the Bowden cable passes through the passage;
    a second jaw element having a second tube abutment surface, a substantially semi-circular cable guide receiving the inner member of the Bowden cable, and a second sliding latch portion for mating with the first sliding latch portion, wherein the inner member has a first end which is held in the mated sliding latch portions so that sliding of the inner member results in selectably positioning the first and second tube abutment surfaces together or spaced apart; and
    an actuator coupled to a second end of the outer tubular casing and a second end of the inner member for applying a force to slide the inner member within the outer tubular casing, the passage, and the cable guide, wherein the Bowden cable substantially isolates the tube being clamped from the weight of the actuator.

2. The clamp system of claim 1 wherein the second jaw element further includes a hollow alignment rod extending generally perpendicular to the second tube abutment surface and slidably mounted in the passage of the first jaw element, wherein the hollow alignment rod is aligned with one end of the cable guide, and wherein the inner member of the Bowden cable passes through the alignment rod.

3. The clamp system of claim 2 further comprising a spring disposed in the passage and bearing against the alignment rod to bias the first and second tube abutment surfaces apart.

4. The clamp system of claim 1 wherein the second sliding latch portion is comprised of an arm with a slot and a latch member slidable within the slot, wherein the latch member is attached to the first end of the inner member of the Bowden cable, and wherein the first sliding latch portion is comprised of a catch for receiving the latch member.

5. The clamp system of claim 4 wherein the arm is comprised of a swing arm for swinging between a closed position generally perpendicular to the second tube abutment surface and an open position to allow a tube to be inserted, and wherein the catch is comprised of a catch groove in the first jaw element.

6. The clamp system of claim 5 wherein the latch member is comprised of a bar extending through the slot, and wherein the bar is releasably captured in the catch groove.

7. The clamp system of claim 4 wherein the second jaw element further includes a hollow alignment rod extending generally perpendicular to the second tube abutment surface and slidably mounted in the passage of the first jaw element, wherein the arm extends generally perpendicular to the second tube abutment surface, and wherein the alignment rod is rotatable in the passage so that the second jaw element is movable to place the arm into an open position to allow a tube to be inserted.

8. The clamp system of claim 7 wherein the catch is comprised of a receptacle and a plunger, and wherein the latch member is comprised of a block with a detent for receiving the plunger.

9. The clamp system of claim 8 wherein the latch member further comprises a set screw for retaining the block in the slot.

10. The clamp system of claim 1 wherein the actuator comprises a motor coupled to the Bowden cable for driving the inner member between an open position and a fully-clamped position.

11. The clamp system of claim 10 wherein the actuator further comprises a user-activated control element for selecting a corresponding position of the inner member.

12. The clamp system of claim 1 further comprising at least one pigtail clip extending from the first jaw element for aligning the tube between the first and second tube abutment surfaces.

* * * * *